United States Patent [19]

Poulsen

[11] 3,934,013
[45] Jan. 20, 1976

[54] PHARMACEUTICAL COMPOSITION

[75] Inventor: Boyd J. Poulsen, Palo Alto, Calif.

[73] Assignee: Syntex (U.S.A.) Inc., Palo Alto, Calif.

[22] Filed: Feb. 21, 1975

[21] Appl. No.: 551,811

[52] U.S. Cl. ............... 424/239; 260/239.55 D
[51] Int. Cl.² ........................ A61K 31/56
[58] Field of Search ................ 424/239, 240; 260/239.55 D

[56] References Cited
UNITED STATES PATENTS

| | | | |
|---|---|---|---|
| 3,073,743 | 1/1963 | Spero | 167/65 |
| 3,472,931 | 10/1969 | Stoughton | 424/240 |

*Primary Examiner*—Elbert L. Roberts
*Attorney, Agent, or Firm*—Tom M. Moran

[57] ABSTRACT

This invention relates to a topical, anti-inflammatory, pharmaceutical composition which comprises (a) a pharmaceutically acceptable solvent, e.g. propylene glycol and water, and (b) at least two corticosteroids chosen from those represented by formulas A through K defined hereinafter, each corticosteroid dissolved in said solvent at a concentration equal to the saturation solubility for each steroid. Other suitable pharmaceutical formulation additives may be added to prepare the desired type of formulation, e.g. cream, ointment, lotion, or gel. The invention includes a process for preparing the compositions and a method for treating inflamed skin conditions using the novel compositions.

50 Claims, No Drawings

PHARMACEUTICAL COMPOSITION

BACKGROUND OF THE INVENTION

1. Field of the Invention

This invention relates to topical anti-inflammatory pharmaceutical compositions which are useful for treating diseases of the skin, particularly inflammatory manifestations of corticosteroid-responsive dermatoses. The composition comprises a suitable pharmaceutical solvent and dissolved therein at least two corticosteroid compounds defined hereinafter, each corticosteroid being present at a specific amount relative to the others. Further, the new compositions of this invention provide improvement in the treatment of inflamed condition of the skin. A new method for the preparation of the compositions of this invention is also disclosed.

2. Prior Art

The direct application of drugs to the skin surface has been used since antiquity to treat diseases of the skin. In general, the skin is an effective barrier to the passage of externally applied agents and most chemical substances penetrate intact skin poorly. Since the pharmacological effect of a drug is dependent on achieving a certain threshold concentration in the viable tissues of the skin, effective therapy requires sufficient percutaneous absorption of the drug to achieve the required tissue concentration levels.

The primary barrier to the precutaneous absorption of drugs has been identified as the stratum corneum, the layer of stratified and keratinized dead cells at the skin surface. The ability of chemical agents or drugs to diffuse across the stratum corneum into the deeper tissues is directly related to the physical chemical properties of the drugs. It is known that certain low molecular weight organic solvents such as acetone, chloroform, and dimethyl sulfoxide penetrate the human skin more readily (i.e. at a faster rate) than most drugs, particularly substances of high molecular weight such as corticosteroids. For such compounds, the therapeutic effectiveness is greatly dependent on the rate of diffusion from the topical vehicle (the base) into the skin, i.e. the penetration rate. Increasing the rate of diffusion is an important mechanism for improving therapeutic effectiveness of many topically applied drugs.

The most obvious and commonly used method for increasing the penetration rate of a topically applied drug is to increase its concentration in the vehicle. There are limitations to this approach that bear directly upon the utility of the present invention. For the greatest proportion of skin diseases requiring topical therapy, the skin is the principal barrier to drug absorption and drug absorption proceeds by the process of passive diffusion. Thus only the concentration of drug actually in solution in the vehicle directly affects the drug penetration rate. For a given vehicle and drug, increasing the drug concentration appreciably beyond the saturation concentration in the vehicle will have only a marginal effect on the rate of percutaneous absorption. Thus in a suspension, i.e. a drug formulation wherein a substantial majority of the drug is present in the pure, undissolved state, very little, if any, increase in absorption rate will be seen from adding more excess drug so long as the skin acts as the primary barrier to drug absorption.

Marcus et al. [*J. Pharm. Sci.*, 54, 495–6 (1965)] have described improved in vitro release into water for mixtures of two steroids. In their report data are present for two different mixtures: dexamethasone plus prednisolone and dexamethasone plus betamethasone. The systems described by Marcus et al. differ completely from those described in the present invention. In the Marcus et al. article an experimental situation is described where release from the vehicle is the rate-limiting step in diffusion instead of diffusion through the skin barrier — the case which normally prevails in the precutaneous absorption of drugs. Marcus et al. describe formulations where the drug is present primarily as suspended solid particles instead of the solubilized systems described in this invention. They also state that rlease is independent of the nature of the vehicle whereas in the present invention vehicle composition must be carefully adjusted depending on the nature and total concentration of the steroid mixture employed. The present invention also requires careful selection of compounds used in a specific vehicle and adjustment of the relative amounts of each steroid according to their saturation solubility. Thus, although an increase in the rate of release of suspended drug into water may be seen, a corresponding rate of penetration of the stratum corneum is not seen using suspension systems because the diffusional resistance of the skin may be any where from 1000 of several million times greater than that offered by water or ointment based vehicles. (See for example Scheuplun, R. J., *Molecular Structure and Diffusional Processes Across Intact Epidermis*, Final Comprehensive Report No. 7, Springfield U.S. Dept. of Commerce, 1966 and Higuchi, W. I., J. Pharm. Sci., Vol 5, pp. 802–4, 1962.)

The limitations inherent in systems where the drug (or drugs) are presented in the form of suspended material in a vehicle has been analyzed by Katz and Poulsen ("Absorption of Drugs Through The Skin" in *Experimental Pharmacology* Ed. B. B. Brodie, pub. Springer Verlag 1971) and by Poulsen ("Design of Topical Drug Product: Biopharmaceutics" in *Drug Design* Vol. 4 Ed. E. J. Ariens, pub. Academic Presd, 1974).

It is known that pregnenolone hemiesters and their salts may be applied topically as a mixture for the treatment of alleviating allergic, pruritic and inflammatory skin conditions. See for example U.S. Pat. No. 3,197,367 issued July 27, 1965 to Panzarella. Not only is this class of compounds completely different from the corticosteroids employed in the composition of this invention, but also a greater percentage of the active ingredients is required for therapeutic activity. It is also mentioned in U.S. Pat. No. 3,743,741 issued July 3, 1973 to Laurent et al. that mixtures of two 9-chloro substituted prednisolones may be used as an ointment. No particular advantage of the mixture over either one alone at an equivalent concentration is discussed, however. The compounds of U.S. Pat. No. 3,743,741 are entirely different than the compounds employed in this invention. Mixtures of 1-dehydrocortisone, 1-dehydrocortisol, and the corresponding 9α-chloro- or fluoro-derivatives are disclosed in U.S. Pat. No. 3,134,718 to Nobile. The compounds of the Nobile patent are entirely different than the compounds useful in the compositions of this invention and the combination of Nobile is not shown to have any particular advantage over a composition having an equivalent concentration of any of the drugs alone. Another mixture of steroids, fluocortolone and fluocortolone caproate, has been marketed by Schering Ag as Ultralan. These compounds and the ratios at which they are employed are entirely different than the mixture of this invention.

I have now discovered that a particular group of corticosteroids when applied as mixtures in a topical vehicle show an increased rate of penetration of the stratum corneum which is greater than any one of the corticosteroids alone at an equivalent concentration. Surprisingly, the total rate of corticosteroid penetration is substantially additive, a result heretofore not shown in the prior art for pharmaceutical solutions. The new composition of this invention, which is in essence a solution, exhibits a greater penetration rate than does a suspension system of similar composition. Thus, not only does the composition of this invention offer the advantage of greater activity, but also because it is in essence a solution of the drug in an acceptable pharmaceutical solvent, the composition is generally a more homogeneous mixture which is not plagued by crystallization problems as suspensions often are. It has also been found that the combination composition of this invention can be adjusted so that the total concentration of the individual drugs used is small enough to reduce the potential for side effects of any of the individual drugs used at a concentration equivalent to the total concentration of each corticosteroid used in the composition of this invention. This results, of course, in a safer drug composition.

SUMMARY OF THE INVENTION

In its broadest aspect this invention is a topical, anti-inflammatory, pharmaceutical composition which comprises a. a pharmaceutically acceptable solvent and b. at least two corticosteroids, each dissolved in the solvent at a concentration equal to the saturation solubility for each corticosteroid, the corticosteroids being chosen from the group represented by the following formulas:

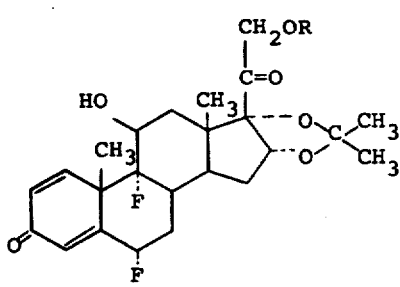

wherein in compound (A) R is

in compound (B) R is H,
in compound (C) R is

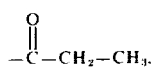

in compound (D) R is

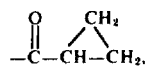

in compound (E) R is

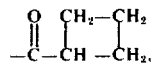

in compound (F) R is

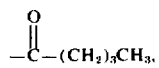

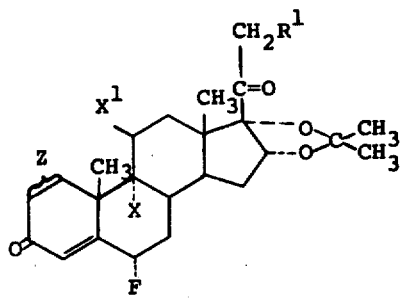

in compound (G) R$^1$ is F; X and X$^1$ both Cl, Z is a double bond,
in compound (H) R$^1$ is OH; X and X$^1$ are both Cl, Z is a double bond,
in compound (I) R$^1$ is OH; X is H and X$^1$ is OH, Z is a single bond,
in compound (J) R$^1$ is

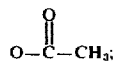

X is H, and X$^1$ is OH, Z is a double bond and compound (K) is

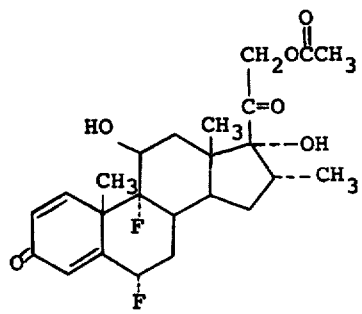

Particularly effective as the solvent in the composition of this invention is a mixture of about 15% by weight or more of a glycol, preferably propylene glycol, and about 85% by weight or less water. Preferably the corticosteroid mixture comprises 3 compounds chosen from the group A,C,D,E, and F, more specifically compounds A,C and D. Other preferred aspects of the composition of this invention will be discussed hereinafter.

Another aspect of this invention is a process of treating inflammatory conditions which process comprises topically administering an effective amount of the composition of this invention.

Still another aspect of this invention is a process for preparing the composition of this invention which process comprises dissolving at least two corticosteroids chosen from the group consisting of those represented by the formulas (A) through (K) discussed hereinafter so that each corticosteroid is dissolved at its saturation solubility concentration, mixing the resulting solution with an effective amount of suitable pharmaceutical formulation additives to prepare a topical, anti-inflammatory, pharmaceutical composition which comprises about 0.001%w to about 0.5%w of said corticosteroids.

PREFERRED EMBODIMENTS

The essence of the invention is utilizing a mixture of active ingredients, steroids, hereinafter defined, each of which has a chemical structure differing from the others but each having similar therapeutic (anti-inflammatory) activities, the steroids being present in solution at specific ratios relative to each other, the ratios being governed at least in part by the concentration of each steroid, which is equal to its saturation solubility in the solvents employed. The mixture is dissolved in a suitable pharmaceutical solvent which may be substantially anhydrous or may be mixed with water, depending on what type of formulation will be used for topical application, i.e. cream, ointment, lotion, gel, or the like. Generally the steroids are more soluble in anhydrous solvents such as a glycol than in a solvent/water mixture and the exact ratio of steroids will be affected by the presence of water, each steroid having its own independent solubility characteristics in each solvent system being employed. The ratios given for compounds found to be useful in this invention [(A) through (K), below] are set by arbitrarily giving compound (A) the value of 1.00 and relating the relative amounts of the other steroids present to compound (A). Each has then a ratio range relative to A and to each other steroid. By employing the steroids in a particular formulation at these ratios, not only is the maximum activity for each compound obtained but also the total activity is greater than any one of the compounds alone at an equivalent concentration.

The specific multisteroid composition of this invention offers certain advantages over comparable single steroid compositions known in the art. (1) The activity, as measured by the rate of total steroid penetration across the stratum corneum is greater for the composition of this invention than for a single steroid composition of equivalent concentration. (2) Because of (1) there appears an enhanced clinical response to the composition of this invention compared to a comparable known formulation having an equivalent concentration of one steroid alone. (3) Reduced doses of the individual steroids may be used due to superior total penetration. (4) The potential for side effects in the target species is reduced because of the lower total dose of drug required. (5) Further, because of flexibility in formulation, topical, anti-inflammatory compositions having low glycol solvent contents to reduce the chance of irritation in users who have an adverse reaction to glycols, such as propylene glycol.

Broadly, the topical, anti-inflammatory, pharmaceutical composition of this invention comprises a. a pharmaceutically acceptable solvent and b. at least two corticosteroids, each dissolved in the solvent at a concentration equal to the saturation solubility for each compound. The corticosteroids are chosen from the group represented by the formulas (A) through (K) presented hereinafter, the total concentration of corticosteroids dissolved being less than about 0.5% by weight of the final pharmaceutical composition and the corticosteroids being present in amounts relative to each other such that the activity, as measured by the total steroid penetration rate across a membrane, such as the stratum corneum, is greater for the mixture than for any of the corticosteroids alone at an equivalent total amount.

A pharmaceutically acceptable solvent is one which (i) is substantially non-toxic and non-irritating under the conditions used, (ii) will dissolve a sufficient amount of the drugs used to give the desired effect, and (iii) may be readily formulated into any of the classical drug formulations such as creams, ointments, lotions, or gels. Particularly suitable solvents include water, glycerin, propylene carbonate, and glycols such as a 1,2-propylene diol (i.e. propylene glycol), 1,3-propylene diol or mixtures thereof; polyethylene glycol having molecular weight of from 100 to 800; dipropylene glycol; etc.; and mixtures of the aforementioned with each other. Preferably the pharmaceutically acceptable solvent will be a glycol, particularly propylene glycol (PG), either alone or admixed with water. A particularly preferred solvent comprises 15% by weight or more of a suitable glycol, preferably PG, and 85% by weight or less water.

The topical, anti-inflammatory pharmaceutical composition of this invention requires that at least two of the corticosteroid, compounds, and preferably no more than 5, be present in solution, the compounds being chosen from those represented by the following structures (A) through (K) in relative amounts shown adjacent the respective structures; each of the drugs being present at concentration in the pharmaceutically acceptable solvent equal to that drug's saturation solubility in the solvent. Preferably the solvent comprises at least 15% by weight (%w) propylene glycol or more and 85% w water or less. The compounds are represented by:

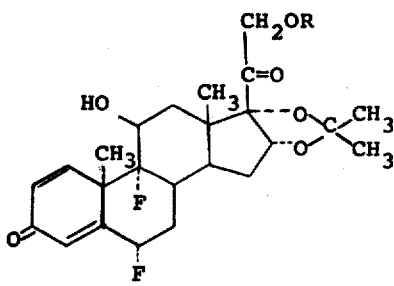

wherein for (A) R is

present at 1.00 relative part;
(B) R is —H present at 22–33 relative parts;
(C) R is

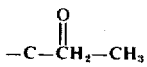

present at 0.17–0.48 relative part;
(D) R is

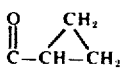

present at 0.14–0.38 relative part;
(E) R is

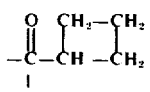

present at 0.32–2.70 relative parts; and
(F) R is

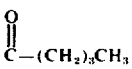

present at 0.13–0.98 relative part;

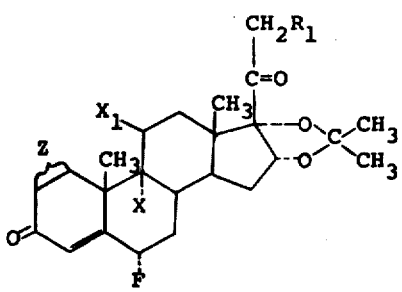

wherein for (G) Z is a double bond, $R_1$ is F and X and $X_1$ and Cl: present at 0.02–0.25 relative part;
(H) Z is a double bond, $R_1$ is OH and X and $X_1$ are Cl: present at 1.50–19.05 relative parts; and
(I) Z is a single bond; $R_1$ is OH, X is H, $X_1$ is OH: present at 54.50–90.48 relative parts;
(J) Z is a double bond, $R_1$ is

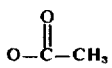

X is H, and $X_1$ is OH present at 0.25–5.00 relative parts;
(K) is

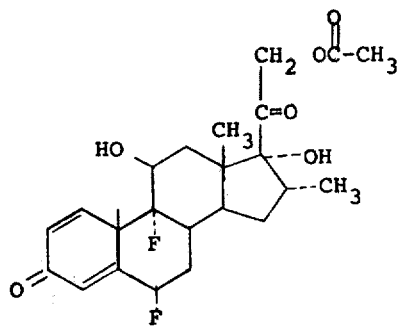

present at 1.60–7.40 relative parts.

Following is the list of compounds A through K with their corresponding common names:

(A) Fluocinonide
(B) Fluocinolone acetonide
(C) Fluocinolone acetonide 21-propionate
(D) Fluocinolone acetonide 21-cyclopropyl carboxylate
(E) Fluocinolone acetonide 21-cyclobutyl carboxylate
(F) Fluocinolone acetonide 21-valerate
(G) 6α, 21-difluoro-9α, 11β-dichloro-16α, 17α-isopropylidenedioxy-1,4-pregnadiene-3, 20-dione
(H) Fluclorolone acetonide
(I) Flurandrenolide (6α-fluoro-16α-hydroxyprednisolone-16, 17-acetonide)
(J) Flunisolide-21-acetate
(K) Flumethasone-21-acetate Compounds A through F, I and J may be prepared by methods known in the art, particularly those disclosed in U.S. Pat. No. 3,126,375 to Ringold, et al. and U.S. Pat. No. 3,014,938 to Mills et al. Compound G may be prepared as disclosed in U.S. Pat. No. 3,409,613 to Fried; compound H by the methods disclosed in U.S. Pat. No. 3,201,391 to Bowers; and compound K by methods shown in J. Am. Chem. Soc. 81, 3156 (1959). As much of these patents or journals as is pertinent is incorporated herein by reference.

In designing the mixtures of this composition it is preferred that the mixture include those compounds from those represented by A through K which have about the same level of solubility. Thus in a formulation which is substantially anhydrous ("substantially anhydrous" meaning less than about 3%w water) employing a pharmaceutically acceptable solvent such as propylene glycol, the following mixtures and ratios are exemplary as effective ratios but are not to be construed as limiting:

| compounds | A/C/D/E/F | 1.00/.42/.38/2.71/.98 |
|---|---|---|
| compounds | D/E/F | .38/2.71/.98 |
| compounds | B/I | 32.10/54.50 |
| compounds | F/H/K | .98/1.50/1.60 |
| compounds | C/D/G/J | .42/.38/.25/.25 |
| compounds | A/C/D | 1.00/.42/.38 |
| compounds | A/F/H/K | 1.00/.98/1.50/1.60 |

On the other hand in a formulation wherein the solvent is substantially water, i.e. about 96%w or more of water with 5%w or less PG the following mixtures and ratios are exemplary, but are not to be construed as limiting:

| compounds | A/C/D/E | 1.00/.31/.24/.56 |
|---|---|---|
| compounds | F/G | .17/.02 |
| compounds | B/H/I | 33.30/19.05/90.48 |
| compounds | H/K | 19.05/7.4 |

-continued

| compounds | B/I | 33.3/90.48 |
|---|---|---|
| compounds | C/D/E | .31/.24/.56 |
| compounds | A/C/D | 1.00/.31/.24 |

In the formulation wherein the solvent is a mixture of about 60%w PG and 40%w water, the following mixtures and ratios are exemplary, but again are not to be construed as limiting:

| compounds | A/C/D/E/F | 1.00/.47/.32/1.47/.39 |
|---|---|---|
| compounds | C/D/F | .47/.32/.39 |
| compounds | A/E | 1.00/1.47 |
| compounds | A/C/D | 1.00/.47/.32 |

The enhanced penetration effects of these combinations may be seen over a wide range of concentrations as long as the drugs are kept at their saturation solubility. Relative to the solvent, the mixture of corticosteroids is dissolved at levels which depend on the particular solvent and may vary from about 1.0 microgram (mg)/milliliter (ml) of solvent to about 10 milligrams (mg)/milliliter of solvent to obtain the increased penetration rate. The mixture of corticosteroids is first dissolved in the solvent then formulated into a composition which may be applied topically as any suitable classical formulation as described in the United States Pharmacopoeia XVII, for example as a (1) cream, (2) ointment, (3) lotion, or (4) gel, the total corticosteroid concentration in the final formulation being a therapeutically effective amount which will generally be between about 0.001 and 0.5%w, preferably less than about 0.2%w but more than about 0.005%w.

It is important to realize that for this composition the corticosteroids are dissolved in the solvent and are at their saturation solubility concentrations, i.e, the maximum amount dissolved in the solvent at a given temperature. Although some of the corticosteroids may be present outside of solution, the presence of excess steroid in the pure form does not significantly enhance the rate of penetration of the composition. In some cases, particularly if the total drug concentration is low, it may be considered advisable for some excess, undissolved drug to be present in order to maintain maximum thermodynamic activity of each drug entity, i.e. to sustain the concentration of each drug at its saturation solubility concentration. However, even though there may be some drug present which is undissolved, the majority of each of the drugs present is in solution.

The group of corticosteroids which are eminently suitable for use in the composition of this invention are those which exhibit about the same level of solubility in the solvent employed. Such a group comprises a mixture of at least 2 of the compounds represented by the formulas A, C—H, J, and K.

Particularly valuable in this regard are mixtures of corticosteroids chosen from the fluocinolone acetonide esters represented by formulas A,C,D,E and F above.

Preferably, this invention is a topical, anti-inflammatory, pharmaceutical composition which comprises a. a suitable pharmaceutical solvent, preferably about 1 to 99.9%w of a mixture of about 15%w or more propylene glycol and 85%w or less water, b. suitable pharmaceutical formulation additives preferably about 0.1 to 99%w; and c. dissolved in the solvent, a mixture of at least 2 corticosteroids chosen from the group consisting of compounds represented by formulas A through K above, preferably formulas A,C,D,E and F, above, each steroid being present at the relative amounts set forth hereinbefore. The total concentration of the steroids in the pharmaceutical composition is 0.001 and 0.5%w, preferably 0.005 and 0.20%w, and even more preferably between about 0.01 to about 0.015%w.

A discussion of representative formulations which utilizes the above solution of corticosteroids and suitable pharmaceutical formulation additives follows below. It is to be understood that in the following discussion "active ingredients" refers to the total amount of the mixture of at least two of compounds A through K present in the particular formulation. Preferably the mixture will contain no more than 5 compounds in solution at the ratios set forth above, and even more preferably will consist of 3 of the compounds, particularly 3 chosen from compounds A,C,D,E, and F.

1. Cream

The topical, anti-inflammatory corticosteroid mixture may be prepared and applied in a cream base, i.e. a semi-solid emulsion of oil in water or water in oil. By definition an emulsion is a two phase system with one liquid (e.g. fats or oils) being dispersed as small globules in the other substance (e.g. the glycol/water solvent phase employed as the primary solvent for the corticosteroid mixture). Typically the cream formulation may contain (other than the solution of corticosteroids) fatty alcohols, surfactants, mineral oil or petrolatum and other typical pharmaceutical adjuvants such as antioxidants, antiseptics, or compatible adjuvants.

The following cream base formulation is representative of the compositions of this invention:

Cream Base

| Ingredient | Operative range(%w) | Preferred range(%w) |
|---|---|---|
| Water/glycol mixture (15% or more glycol) | 55 – 99 | 75 – 95 |
| Fatty alcohol | 1 – 20 | 5 – 10 |
| Non-ionic Surfactant | 0 – 10 | 0.1 – 5 |
| Mineral oil | 0 – 10 | 0 – 8 |
| Typical pharmaceutical adjuvants | 0 – 5 | 0 – 2 |
| *Active Ingredients | 0.001 – 0.5 | 0.005 – 0.20 |

In general the fatty alcohol ingredient in the cream composition can be any fatty alcohol having from 16 to 24 carbons or mixtures thereof and is preferably a saturated, monohydric primary alcohol. Suitable fatty alcohols include cetyl alcohol, stearyl alcohol, behenyl alcohol and the like. Vehicles having excellent properties are prepared using stearyl alcohol or mixtures of cetyl and stearyl alcohol as the fatty alcohol component.

The concentration of the fatty alcohol ingredients may vary between about 1 to about 20 percent by weight(%w) of the final, formulated composition. Preferably the fatty alcohol will be present in amounts of about 5 to 10%w.

The cream formulation useful to apply the steroid combination of this invention usually will also contain an effective amount of a surfactant. An effective amount is enough to assist in maintaining homogeneity of the vehicle and preventing exudation or bleeding of the more liquid components of the vehicle such as the glycol solvent upon prolonged storage at elevated temperatures. Thus, the vehicle contains a quantity of the surfactant sufficient to prohibit visible exudation of the more liquid components from the vehicle after storage at 45° for 48 hours. In some instances the amount of surfactant required may be small. No more of the surfactant is used than is needed to prevent this exudation. Excess quantities are undesirable because other ingredients and their functions are needlessly diluted. If the surfactant concentration is not carefully balanced with the other components, stability of the medicant vehicle after one or more repeated cycles of solidification (by cooling) in liquification (by heating), that is the freeze/thaw ability is impaired. Thus, an effective amount of surfactant will be within the range of from 0 to 10%w of the final, formulated composition, preferably about 0.1 to 5%w will be used.

The surfactant may be anionic, cationic, or nonionic, preferably nonionic. Suitable surfactants include saturated fatty acids having from 16 to 24 carbons such as stearic acid, palmitic acid, and behenic acid; fatty amides such as oleamide, palmitamide, stearamide, and behenamide; and esters of fatty acids having from 16 to 24 carbons such as sorbitan monostearate, polyethylene glycol monostearate, propylene glycol monostearate, and the corresponding monoesters of other fatty acids such as oleic acids and palmitic acids. Best results are achieved particularly with the esters if the fatty group of the coupling agent and fatty alcohol is the same or approximately the same number of carbons. It is essential that the fatty acids be saturated and the fatty acids or amides by substantially free from irritating amounts of acids or amides having fewer than 16 carbons.

Particularly valuable as surfactants are the nonionic surfactants referred to as Span and Tween. The Span type materials are partial esters of common fatty acids (lauric, palmitic, stearic, and oleic) and hexitol anhydrides (hexitans and hexides), derived from sorbitol. The Tween Type materials are derived from the Span products by adding polyoxyethylene chains to the nonesterified hydroxyls. Particularly valuable are Span 60, Span 80, and Tween 60 (Available through Atlas Chemical Co.).

A further component of a typical oil/water emulsion cream base is an effective amount of mineral oil, also referred to as mineral petrolatum, i.e. about 0 to 10%w, preferably about 1 to 8%w.

The cream will also include a pharmaceutically acceptable glycol solvent such as discussed above. preferably this glycol solvent will be a propylene glycol (PG)/water mixture which is 15%w PG or more, even more preferably about 30% PG but no more than 60%w PG, the mixture being present at 55–99%w, preferably 70–95%w of the total cream base formulation. The glycol solvent and the fatty alcohol ingredients are the principal components in the preferred composition of the invention, the glycol solvent being the primary solvent for the corticosteroids used in the formulation although other adjuvants present such as the surfactants may also contribute significantly to the drug solubility. The fluidity of the composition increases with increased concentrations of the glycol solvent, while the fatty alcohol forms a protective, lubricant and occlusive film.

Other typical pharmaceutical adjuvants may be included as well; for example, antiseptics such as thimerosal, a pharmaceutically acceptable antioxidant such as citric acid; and other additives conventionally used to improve consistency, homogeneity, spreadability, texture, and appearance of the vehicle or it's residual film. The latter can be used to give a residual film varying degrees of continuity, flexibility, adhesion, occlusion, water repellancy, washability and the like. Examples of typical adjuvants include surfactants such as natural gums including agar, acacia gum, guar gum, tragacanth, and the like; cellulose derivatives including cellulose ethers such as methyl cellulose, ethyl cellulose, carboxymethyl cellulose, and the like; starch and starch derivatives, and water soluble vinyl polymers such as polyvinylpyrrolidone, polyvinyl alcohol, vinylpyrrolidonevinyl alcohol copolymers, and the like. Nonessential ingredients may be present at levels that vary from 0 to 5%w, but preferably less than about 1% will be present.

2. Ointment

The topical, anti-inflammatory corticosteroid mixtures of this invention may also be applied as an ointment, preferably a classical ointment. Generally, a "classical" ointment is a semi-solid anhydrous composition which may contain mineral oil, white petrolatum, a suitable solvent such as the glycol solvents recited hereinbefore (including propylene carbonate), and other pharmaceutically acceptable additives such as surfactants, e.g. Span, Tween, or wool fat (lanolin), stabilizers such as antioxidants (e.g. citric acid), and other adjuvants as mentioned above. Following is a preferred, classical ointment base formulation suitable for applying the topical anti-inflammatory corticosteroid mixture of this invention:

| Ingredient | Classical Ointment Base Operable range(%w) | Preferred range(%w) |
|---|---|---|
| White petrolatum | 45 – 94 | 75 – 90% |
| Mineral oil | 5 – 20 | 5 – 10% |
| Glycol solvent | 1 – 15 | 2 – 8% |
| Surfactant | 0 – 10 | 0.5 – 5% |
| Stabilizer | 0 – 10 | 0.1 – 2% |
| Active Ingredients | 0.001 – 0.5 | 0.005 – 0.2 |

Other suitable ointment base formulations which contain propylene carbonate are described in a co-pending U.S. patent applications Ser. No. 85,246, filed Oct. 29, 1970 by Shastri et al. entitled "Propylene Carbonate Ointment Vehicle" and Ser. No. 201,997, filed Nov. 24, 1971 by Chang et al. entitled "Fatty Alcohol-Propylene Carbonate-Glycol Solvent Cream Vehicle." As much of those applications as is pertinent is incorporated herein by reference. Following is an ointment base formulation containing propylene carbonate found to be particularly effective for the compositions of this invention:

| Ingredient | Propylene Carbonate Ointment Base Operable range(%w) | Preferred range(%w) |
|---|---|---|
| Active Ingredients | 0.001 – 0.5 | 0.005 – 0.2 |
| Propylene Carbonate | 1 – 10 | 1 – 4 |
| Solvent | 1 – 10 | 2 – 6 |
| Surfactant | 1 – 10 | 1 – 5 |
| White Petrolatum | 70 – 97 | 85 – 96 |

The surfactant may be any suitable surfactant discussed hereinbefore while the solvent is preferably a compatible glycol solvent as discussed previously.

A suitable "non-classical" anhydrous, water washable "ointment type" base is described in U.S. Pat. No. 3,592,930 to Katz and Neiman, and as much of that disclosure as is pertinent is incorporated herein by reference. A composition of this invention utilizing such a base is as follows:

| Ingredient | Water-Soluble Ointment Base Operable range(%w) | Preferred range(%w) |
|---|---|---|
| Glycol solvent | 45 – 85 | 55 – 80 |
| Fatty alcohol | 15 – 45 | 20 – 35 |
| Compatible plasticizer | 0 – 15 | 2 – 10 |
| Compatible coupling Agent | 0 – 15 | 1 – 5 |
| Penetrant | 0 – 20 | 0 – 10 |
| Active Ingredients | 0.001 – 0.5 | 0.005 – 0.20 |

The fatty alcohols which are suitable have been previously disclosed above in this specification and in U.S. 3,592,930. As much of those disclosures as is pertinent is incorporated herein by reference. Effective amounts are set forth in the table immediately above.

The glycol solvent has been described hereinbefore and is preferably propylene glycol alone.

The composition can also contain an effective amount of a compatible plasticizer such as polyethylene glycol having a molecular weight of from above 800 to 20,000, 1,2,6-hexanetriol, sorbitol, glycerol, and the like. The plasticizer maintains homogeneity in the fatty alcohol-glycol solvent mixture at ambient temperatures, that is, temperatures at which the fatty alcohol is naturally a solid. This component also improves the plasticity and uniformity of medicant mixtures with the vehicle and provides to the vehicle smoothness and a more pleasing "feel," hence the vehicle containing the plasticizer is more aesthetically acceptable.

The term "compatible" is defined herein to indicate a component which will not cause separation (loss of homogeneity) of the other components, that is, the fatty alcohol and glycol solvent at temperatures up to 45°C.

The plasticizer concentration can be within the range of from 0 to 15 percent. Concentrations above 15 percent may provide a composition which has a consistency unsuitable for normal applications or cause instability of the vehicle mixture and some separation of the components. In general, the particular plasticizer concentration necessary to provide a desired consistency, degree of smoothness and plasticity will vary with the choice of the fatty alcohol component, the choice of glycol solvent, and the ratio of these components in the vehicle.

The particular concentration of plasticizer which will provide the most stable composition will depend upon the choice and concentration of the other ingredients. Preferably, the plasticizer concentration should be balanced so the vehicle has freeze-thaw stability, i.e., does not separate after repeated cycles of solidification (by cooling) and liquefaction (by heating).

The vehicle of this invention can also contain a compatible, pharmaceutically acceptable coupling agent, the term compatible having the above-defined meaning. Suitable coupling agents include saturated fatty acids, fatty amides, and fatty acid esters discussed hereinbefore under suitable surfactants for creams.

The penetrants increase the penetration and therapeutic activity of the medicants and are usually solvents or cosolvents for the medicants. The penetrants can be used in concentrations which are pharmaceutically acceptable for the intended use not to exceed 20 percent of the weight of the vehicle. Representative examples of penetrants include dimethylsulfoxide, dimethylacetanide, dimethylformamide, and the like.

It should be understood that the medicant vehicles of this invention can also contain non-essential ingredients as discussed hereinbefore under the section entitled creams.

The vehicle base of U.S. Pat. No. 3,592,930 does not contain any significant quantity of petrolatum or mineral oil. It is therefore not a classical ointment and is not water-insoluble. It is preferably anhydrous, but can contain minor amounts of water such as up to 3 percent water. The water concentration should not be sufficient to cause separation of the other vehicle components or precipitant medicants dissolved in the vehicle.

The vehicles of this invention can be made from the above ingredients by thoroughly mixing them at ambient or elevated temperatures. Preferably, the active ingredients are first dissolved in the glycol solvent, the components are thoroughly mixed while each is in a liquid state, and the mixture is cooled with good agitation to room temperature. Good agitation is provided until the mixture cools to room temperature.

If desired, additional mechanical agitation and/or shock cooling steps can be used as intermediate or final steps in the manufacturing process to impart more homogeneity or improve texture. Processing equipment suitable for these steps is known and includes heat exchangers, propeller mixers, colloid mills, homogenizers, roller mills, and the like.

3. Lotion

The corticosteroid mixtures of this invention may also be applied as a lotion which is a liquid suspension or dispersion of the active ingredient in water. Generally, along with a glycol/water mixture the lotion will also employ surfactants and fatty acid esters such as those set forth above in the discussion of a cream formulation, along with stabilizers such as an antioxidant and other adjuvants to improve the aesthetics of the lotion.

A particularly suitable glycol/water solvent mixture will be about 15 to 60%w glycol, preferably the glycol is propylene glycol present at a level of no more than 45%w of the mixture. The remainder of the glycol/water mixture will be water, i.e. 40 to 85%w and preferably at least 55%w will be water. A typical formulation of an acceptable lotion base which is usable in the application of the steroid mixtures of this invention is given as follows:

| Ingredient | Lotion Base Operative range(%w) | Preferred range(%w) |
|---|---|---|
| Glycol/water solvent | 69.5 – 99.8 | 94.8 – 99.0 |
| Surfactant | 0.10 – 10 | 0.5 – 2.0 |
| Fatty esters | 0.10 – 10 | 0.5 – 2.0 |
| Stabilizer | 0 – 10 | 0.001 – 1 |
| Active ingredients | 0.001 – 0.5 | 0.005 – 0.20 |

4. Gel

The corticosteroid mixtures of this invention may also be applied topically as a gel, that is, a solution of the drug in a colloidal gel. Typical gelling agents used to prepare pharmaceutically acceptable gels include bentonite, cellulose derivatives such as methyl cellulose and carboxymethyl cellulose, tragacanth, gelatin and, preferably, carboxypolymethylene, e.g. CARBOPOL. The glycol/water mixture is preferably propylene glycol/water with about 20%w glycol to about 90%w glycol, and is even more preferably at least about 60%w glycol. The following is a representative formulation of the gel formulations of this invention:

| Ingredient | Gel Base Operable range(%w) | Preferred range(%w) |
|---|---|---|
| Glycol/water mixture | 90 – 99.9 | 98 – 99.50 |
| Gelling Agent | 0.1 – 10 | 0.5 – 2.0 |
| Active ingredients | 0.001 – 0.50 | 0.010 – 0.20 |

The cream, ointment, lotion, and gel formulations discussed above may be modified to include a therapeutically effective amount of an antibiotic such s penicillin, tetracycline, oxytetracycline, neomycin, gramicidin, chlorotetracycline, erythromycin, and other antibiotics known in the art, or mixtures thereof. An effective amount is whatever amount is needed to effectively reduce bacterial or fungal infections which may accompany an inflamed condition which is being treated using the corticosteroid mixture of this invention. This generally is about 0.1 to 1.0%w of the final formulation, preferably about 0.2 to about 0.5%w.

Thus, it may be seen that another aspect of this invention is an improved process of treating an inflammatory condition in animals, particularly human beings, which process comprises administering a therapeutically effective amount of an appropriate composition of this invention as described hereinbefore and those set forth in the composition claims.

Still another aspect of this invention comprises a process for preparing the unique compositions of this invention. This process comprises a. dissolving at least two corticosteroids chosen from the group represented by formulas (A) through (K) in a suitable pharmaceutical solvent so that each corticosteroid is present in solution at the saturation solubility for each corticosteroid and b. mixing said solution from (a) with an effective amount of suitable pharmaceutical formulation additives to form a topical pharmaceutical formulation which comprises about 0.001 to about 0.5%w of said corticosteroids.

An effective amount of suitable formulation additives is whatever amount is needed to form the type of formulation desired such as a cream, ointment, lotion, gel, and the like. This amount may vary from about 0.1 to about 99%w of the final formulation, while the solvent may vary from about 1%w of the formulation to about 99.9%w of the final formulation.

Generally, the corticosteroids will be dissolved in the solvent at elevated temperatures, e.g. 40°C to 90°C, then the formulation additives are mixed together at elevated temperatures such as 40°C to 90°C. After these individual components are prepared, they are then comixed thoroughly at elevated temperatures, again about 40°C to 90°C and cooled to ambient temperatures with constant agitation.

The following Examples are presented to further show specific, representative pharmaceutical formulations which are part of this invention and to distinguish the multisteroid compositions of this invention over those single-steroid compositions known in the art. The formulations are presented showing the % weight of each of the components, including the compounds. The relative amounts of each compound with reference to compound A as 1.00 are not given in the examples, but each compound is present in relative amounts as set forth hereinbefore. The examples are presented as illustrative only and are not to be construed in a limiting manner.

EXAMPLE 1:

Gel Formulations

An experiment was run to determine the in vitro skin penetration of gel composition of this invention which is representative of the gel base formulation discussed hereinbefore. The composition of this invention included compounds A,C, and D at 0.012, 0.0056 and 0.0045%w, respectively, making a total steroid concentration of 0.0221%w. The penetration of the mixture was compared to the same total concentration, that is, 0.0221%w of each of the individual components. The results show that at all sampling times the mixture gave a greater total drug penetration than did any of the individual components alone. The results are presented in Table 1.

| | The following formulations were prepared | | |
|---|---|---|---|
| I | (Composition of the Invention) | | |
| | compound A | 0.012 | %w |
| | compound C | 0.0056 | |
| | compound D | 0.0045 | |
| | CARBOPOL | 0.50 | |
| | 70%w PG/30%w water qs. ad. | 100.00 | |
| II | (Prior Art Composition) | | |
| | compound A | 0.0221 | %w |
| | CARBOPOL | 0.50 | |
| | 70%w PG/30%w H₂O qs. ad. | 100.00 | |
| III | (Prior Art Composition) | | |
| | compound C | 0.0221 | %w |
| | CARBOPOL | 0.50 | |
| | 70% PG/30% H₂O qs. ad. | 100.00 | |
| IV | (Prior Art Composition) | | |
| | compound D | 0.0221 | %w |
| | CARBOPOL | 0.50 | |
| | 70% PG/30% H₂O qs. ad. | 100.00 | |

The in vitro penetration of each of the compositions I-IV through whole thickness human skin was determined by the method described by Coldman, et al, J. Pharm. Sci., 58, 1098 (1969). The results are set forth in TABLE 1 and shown clearly that the total penetration of a composition of this invention (mixture 1) is greater than any of the prior art compositions at equivalent concentrations.

TABLE I

| Composition | In Vitro Skin Penetration Total Penetration (ng) at hours | | | | | | |
|---|---|---|---|---|---|---|---|
| | 65.5 | 113.5 | 161.5 | 233.5 | 268 | 318.1 | 370 |
| I (Invention) | 48.3 | 236 | 749 | 1931 | 2411 | 2912 | 3465 |
| II (Art) | 40.2 | 134 | 401 | 939 | 1156 | 1357 | 1700 |
| III (Art) | 24.6 | 115 | 293 | 629 | 766 | 911 | 1056 |
| IV (Art) | 11.4 | 52.6 | 207 | 608 | 758 | 913 | 1054 |

Similar results may be obtained employing the following representative gel compositions of this invention.

| Composition V | | |
|---|---|---|
| compound A | .00565 | %w |
| compound C | .00264 | |

-continued

|  |  |
|---|---|
| compound D | .0017 |
| CARBOPOL | 0.50 |
| 60%w PG/40%w Water qs. ad. | 100.00 |
| Composition VI |  |
| compound A | 0.0290 %w |
| compound C | 0.0134 |
| compound D | 0.0108 |
| CARBOPOL | 0.50 |
| 80%w PG/20%w Water qs. ad. | 100.00 |
| Composition VII |  |
| compound C | 0.0134 %w |
| compound D | 0.0108 |
| compound F | 0.018 |
| CARBOPOL | 0.50 |
| 80%w PG/20%w Water qs. ad. | 100.00 |

Other mixtures of corticosteroids A through K, particularly A, C, D, E and F, may be prepared with similar results.

EXAMPLE 2

Cream Base Formulations

A particularly valuable cream base formulation representative of those discussed hereinbefore is given as follows:

| Cream Base A |  |
|---|---|
| Stearyl Alcohol | 15.0 g. |
| Span 60 | 2.0 g. |
| Tween 60 | 2.0 g. |
| Mineral Oil | 3.0 g. |
| Citric Acid | 0.01 g. |
| PG/Water | 77.99 g. |

The proportion of water in the PG/water mixture may be varied from about 85%w or more to less than 10%w, but preferably will be about 80 to about 40%w water (thus the PG/water mixture will be about 15 to 90%w PG, preferably about 20 to 60%w PG).

| Composition X |  |
|---|---|
| compound A | 3.52 mg. |
| compound C | 2.11 mg. |
| compound E | 6.64 mg. |
| cream base A (with PG/water mixture 60%w PG/40%w water) qs. ad. | 100.00 g. |
| Composition XI |  |
| compound A | .288 mg. |
| compound C | .048 mg. |
| compound D | .041 mg. |
| compound E | .091 mg. |
| compound F | .037 mg. |
| cream base A (with PG/water mixture 20%w PG/80%w water) qs. ad. | 100.00 g. |
| Composition XII |  |
| compound A | 3.52 mg. |
| compound C | 2.11 mg. |
| compound D | 1.42 mg. |
| compound E | 6.64 mg. |
| compound F | 1.80 mg. |
| cream base A (with PG/water mixture 60%w PG/40%w water) qs. ad. | 100.00 g. |

Compositions VIII through XII will show a greater penetration rate than any of the corticosteroids alone in the same cream base A at an equivalent concentration. Other representative cream formulations may be prepared using compounds A through K. The procedure for preparing the representative cream base composition of this invention is as follows:

1. The desired amount of the active ingredients (about 0.001 to 0.5% of the total formulated composition) is dissolved in the PG/water solution and heated to 65°–70°C.

2. The stearyl alcohol, Span 60, Tween 60, Mineral oil and citric acid are combined and heated to 65°–70°C.

3. The aqueous phase (1) is added to the oil phase (2) with moderate stirring and the resulting formulation cooled to 30°–35°C.

The following representative formulations are preferable cream formulations of this invention and are prepared as described above:

| Composition VIII |  |
|---|---|
| compound A | .288 mg. |
| compound C | .048 mg. |
| compound E | .091 mg. |
| cream base A (with PG/water mixture 20%w PG/80%w water) qs. ad. | 100.00 g. |
| Composition IX |  |
| compound A | .800 mg. |
| compound E | .360 mg. |
| compound F | .472 mg. |
| cream base A (with PG/water mixture 40%w PG/60%w water qs. ad. | 100.00 g. |

EXAMPLE 3

Water-washable Ointment Base Formulation

A particularly valuable representative anhydrous, water-washable ointment base formulation follows:

| Ointment Base A |  |
|---|---|
| Cetyl alcohol | 1.75 g. |
| Stearyl alcohol | 19.25 g. |
| PEG 6000 | 5.00 g. |
| PG | 74.00 g. |

The procedure for preparing a composition of this invention is as follows:

1. The desired amount of each of the corticosteroids is dissolved in the PG at about 80°–85°C.

2. The cetyl alcohol, stearyl alcohol and PEG 6000 are mixed thoroughly at 80°–85°C.

3. The PG solution (1) is added to the fatty alcohol/PEG mixture and mixed at 90°–95°C for 30 minutes, then cooled slowly to room temperature with good agitation.

The following representative compositions of this invention are prepared as described above:

| Composition XIII |  |
|---|---|
| compound C | 48.1 mg. |
| compound D | 39.0 mg. |
| compound F | 101.0 mg. |
| Ointment base A (qs. ad.) | 100.00 g. |
| Composition XIV |  |
| compound A | 103.0 mg. |
| compound C | 48.1 mg. |
| compound D | 39.0 mg. |
| Ointment base A (qs. ad.) | 100.00 g. |

Compositions XIII – XIV will show a greater penetration rate than any of the corticosteroids alone in the same ointment base at an equivalent concentration. Other mixtures of compounds A through K, particularly A,C,D,E, or F may similarly be prepared.

EXAMPLE 4

Cream Base Formulation

A particularly valuable cream formulation is set forth below: composition XV

Composition XV

| compound A | 0.0082 g. |
| --- | --- |
| compound C | 0.0039 |
| compound D | 0.0029 |
| Cetyl Alcohol | 4.00 |
| Stearyl Alcohol | 4.00 |
| Tween 60 | 2.00 |
| Span 60 | 2.00 |
| Mineral Oil (MO 15) | 5.75 |
| Propylene Glycol | 30.00 |
| Purified Water (qs. ad.) | 100.00 |

PROCEDURE

1. Dissolve drugs in propylene glycol with moderate heating (40°–50°C). Heat to 70°–75°C.
2. Combine cetyl alcohol, stearyl alcohol, tween 60, span 60, and mineral oil and heat to 70°–75°C.
3. Add aqueous phase (1) to oil phase (2) with stirring on Lightnin mixer to form an emulsion and cool to 30°–35°C in water bath with stirring.

Compositions similar to composition XV may be prepared using mixtures of 2 to 5, especially 3, of the corticosteroids represented by formulas A through K, particularly those represented by formulas A,C,D,E and F. Improved penetration rates will be seen along with enhanced therapeutic response.

EXAMPLE 5

Classical Ointment Base Formulations

Representative of a classical ointment base formulation follows:

Composition XVI

| compound A | .0112 %w |
| --- | --- |
| compound C | .0042 |
| compound F | .0110 |
| Mineral Oil | 8.00 |
| Propylene glycol | 8.00 |
| Tween 60 | 2.00 |
| Span 60 | 2.00 |
| White Petrolatum qs. ad. | 100.00 |

PROCEDURE

1. Dissolve drugs in PG at 40°–50°C
2. Combine Mineral oil, Tween, Span and White petrolatum and heat to about 50°C.
3. Combine 1 with 2 with stirring on a "Lightnin" mixer and cool slowly to room temperature.

Similarly, other ointment based formulations may be prepared using mixtures of 2 to 5, preferably 3, compounds A through K, especially 3 member combinations of A,C,D,E, and F.

EXAMPLE 6

CREAM FORMULATION WITH ANTIBIOTICS

The formulations of Examples 1 through 5 may be modified to include a therapeutically effective amount of an antibiotic such as penicillin, tetracycline, oxytetracycline, neomycin gramicidin, chlorotetracycline, erythromycin, and other antibiotics known in the art. Particularly valuable in this regard are the following cream base formulations which are prepared in a manner similar to Example 4.

| Composition XVII | |
| --- | --- |
| compound A | 0.0082 g. |
| compound C | 0.0039 |
| compound D | 0.0029 |
| Neomycin base (as sulfate) | 0.3500 |
| Cetyl Alcohol | 4.0000 |
| Stearyl Alcohol | 4.0000 |
| Tween 60 | 2.0000 |
| Span 60 | 2.0000 |
| Mineral Oil (MO15) | 5.7500 |
| Propylene glycol | 30.0000 |
| Purified water qs. ad. | 100.0000 g. |
| Composition XVIII | |
| compound A | 0.0082 g. |
| compound C | 0.0039 |
| compound D | 0.0029 |
| Neomycin base (as sulfate) | 0.2875 |
| Gramicidin | 0.0275 |
| Mystatin | 12×10⁶ I.U. |
| Cetyl Alcohol | 4.0000 |
| Stearyl Alcohol | 4.0000 |
| Tween 60 | 2.0000 |
| Span 60 | 2.0000 |
| Mineral Oil | 5.7500 |
| Propylene glycol | 30.0000 |
| Purified Water qs. ad. | 100.0000 g. |

Compositions similar to compositions XVII and XVIII may be prepared using mixtures of 2 to 5, especially 3, of the corticosteroids represented by formulas A through K, particularly formulas A,C,D,E, and F.

I claim as my invention:

1. A topical, anti-inflammatory, pharmaceutical composition which comprises
   a. a pharmaceutically acceptable solvent and
   b. at least two corticosteroids, each dissolved in said solvent at a concentration equal to the saturation solubility for each corticosteroid, said corticosteroids being chosen from the group represented by the following formulas:

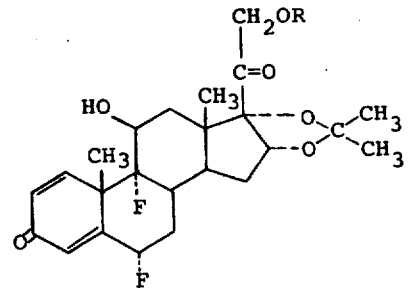

wherein in compound (A) R is

in compound (B) R is H,
in compound (C) R is

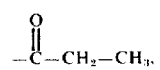

in compound (D) R is in compound (E) R is $$-\overset{O}{\underset{}{C}}-\underset{}{CH}-CH_2\underset{}{\overset{CH_2}{\diagdown}}CH_2,$$

in compound (F) R is $$-\overset{O}{\underset{}{C}}-\underset{}{CH}-\underset{}{CH_2}\overset{CH_2-CH_2}{\underset{}{\diagdown}}CH_2,$$

$$-\overset{O}{\underset{}{C}}-(CH_2)_3CH_3$$

[Structural formula of steroid with substituents $CH_2R^1$, $CH_3$, $X^1$, $Z$, $X$, F]

in compound (G) $R^1$ is F; X and $X^1$ both Cl, Z is a double bond;
in compound (H) $R^1$ is OH; X and $X^1$ are both Cl, Z is a double bond;
in compound (I) $R^1$ is OH; X is H and $X^1$ is OH, Z is a single bond;
in compound (J) $R^1$ is $$O-\overset{O}{\underset{}{C}}-CH_3;$$

X is H, and $X^1$ is OH, Z is a double bond; and compound (K) is

[Structural formula of steroid with $CH_2OCCH_3$, $CH_3$, OH, $CH_3$, HO, F, O]

2. The composition of claim 1 wherein said solvent comprises a mixture of 15%w or more of a glycol and 85%w or less water.

3. The composition of claim 2 wherein said glycol is propylene glycol.

4. The composition of claim 3 wherein said corticosteroids are chosen from the group consisting of compounds A,C,D,E, and F.

5. The composition of claim 4 which comprises a mixture of three of said corticosteroids.

6. A topical, anti-inflammatory, pharmaceutical composition which comprises
 a. a pharmaceutically acceptable solvent;
 b. suitable pharmaceutical formulation additives;
 c. at least two corticosteroids, each dissolved in said solvent at a concentration equal to the saturation solubility for each corticosteroid, said corticosteroids being chosen from the group consisting of those represented by the following formulas,

[Structural formula of steroid with $CH_2OR$, $CH_3$, HO, $CH_3$, O, $CH_3$, $CH_3$, F, F]

wherein in compound (A) R is $$-\overset{O}{\underset{}{C}}-CH_3$$

in compound (B) R is H
in compound (C) R is $$-\overset{O}{\underset{}{C}}-CH_2-CH_3$$

in compound (D) R is $$-\overset{O}{\underset{}{C}}-\underset{}{CH}-CH_2\overset{CH_2}{\underset{}{\diagdown}}$$

in compound (E) R is $$-\overset{O}{\underset{}{C}}-\underset{}{CH}-\underset{}{CH_2}\overset{CH_2-CH_2}{\underset{}{\diagdown}}$$

in compound (F) R is $$-\overset{O}{\underset{}{C}}-(CH_2)_3CH_3$$

[Structural formula of steroid with $CH_2R^1$, $CH_3$, $X^1$, $Z$, $X$, F]

in compound (G) $R^1$ is F; X and $X^1$ are both Cl; Z is a double bond in compound (H) $R^1$ is OH; X and $X^1$ are both Cl; Z is a double bond in compound (I) $R^1$ is OH; X is H; and $X^1$ is OH; Z is a single bond in compound (J) $R^1$ is $$O-\overset{O}{\underset{\|}{C}}-CH_3;$$

X is H; and $X^1$ is OH; Z is double bond and compound (K) is

[chemical structure diagram showing steroid with substituents $CH_2OCCH_3$, C=O, $CH_3$, HO, OH, $CH_3$, F, O, F]

said corticosteroids being present at a total concentration of about 0.001% by weight to about 0.5% by weight.

7. The composition of claim 6 wherein said corticosteroids are present in the relative amounts shown in the following list:
compound A present at 1.00 relative part
compound B present at 22 – 33 relative parts
compound C present at 0.17 – 0.48 relative part
compound D present at 0.14 – 0.38 relative part
compound E present at 0.32 – 2.70 relative parts
compound F present at 0.13 – 0.98 relative part
compound G present at 0.020 – 0.25 relative part
compound H present at 1.50 – 19.05 relative parts
compound I present at 54.50 – 90.48 relative parts
compound J present at 0.25 – 5.00 relative parts
compound K present at 1.60 – 7.40 relative parts 8. The composition of claim 6 wherein said solvent is a mixture comprising about 15% by weight glycol or more and 85% by weight or less water.

9. The composition of claim 8 wherein said glycol is propylene glycol.

10. The composition of claim 9 wherein said group consists of corticosteroids represented by formulas A,C,D,E,F,G,H,J and K.

11. The composition of claim 10 wherein said group consists of corticosteroids represented by formulas A,C,D,E and F.

12. The composition of claim 11 wherein 3 corticosteroids are present in said composition.

13. The composition of claim 8 which comprises
  a. about 1.0 to 99.9% by weight of said pharmaceutically acceptable solvent, wherein said glycol is propylene glycol;
  b. about 0.1 to 99% by weight suitable pharmaceutical additives, and
  c. about 0.005 to about 0.20% by weight of said corticosteroid mixture.

14. The composition of claim 6 which is a cream formulation comprising
  a. about 55 to 99% by weight a solvent comprising (i) 15% by weight or more of a glycol and (ii) 85% by weight or less water;
  b. about 1 to 20% by weight fatty alcohol;
  c. about 0 to 10% by weight non-ionic surfactant;
  d. about 0 to 10% by weight mineral oil;
  e. about 0 to 5% by weight other typical pharmaceutical adjuvants; and
  f. about 0.001 to 0.5% by weight of a mixture of from 2 to 5 of said corticosteroids.

15. The composition of claim 14 which comprises
  a. about 75 to 95% by weight of a solvent comprising (i) about 15 to 60% by weight propylene glycol and (ii) about 40 to 85% by weight water;
  b. about 5 to 10% by weight fatty alcohol;
  c. about 0.1 to 5% by weight non-ionic surfactant;
  d. about 0 to 8% by weight mineral oil;
  e. about 0 to 2% by weight other typical pharmaceutical adjuvants; and
  f. about 0.005 to 0.20% by weight of a mixture of from 2 to 5 corticosteroids chosen from the group represented by formulas A, C, D, E and F.

16. The composition of claim 15 wherein said mixture of corticosteroids comprises A, C and D.

17. The composition of claim 15 which includes an effective amount of an antibiotic.

18. The composition of claim 6 which is an ointment formulation comprising
  a. about 45 to 94% by weight white petrolatum;
  b. about 5 to 20% by weight mineral oil;
  c. about 1 to 15% by weight pharmaceutically acceptable solvent;
  d. about 0 to 10% by weight pharmaceutically acceptable surfactant;
  e. about 0 to 10% by weight stabilizer;
  f. about 0.001 to 0.5% by weight of a mixture of from 2 to 5 of said corticosteroids.

19. The composition of claim 18 which comprises
  a. about 75 to 90% by weight white petrolatum;
  b. about 5 to 10% by weight mineral oil;
  c. about 2 to 8% by weight propylene glycol;
  d. about 0.5 to 5% by weight surfactant;
  e. about 0.1 to 2% by weight stabilizer
  f. about 0.005 to 0.2% by weight of a mixture of from 2 to 5 corticosteroids chosen from the group consisting of those represented by formulas A, C, D, E and F.

20. The composition of claim 19 wherein said mixture of corticosteroids comprises those represented by formulas A, C and D.

21. The composition of claim 18 which includes an effective amount of an antibiotic.

22. The composition of claim 6 which is a gel formulation comprising
  a. about 90 to 99.9% by weight of a suitable solvent comprising about 15 to 90% by weight of a pharmaceutically acceptable glycol and about 10% to 85% by weight water;
  b. about 0.1 to 10% by weight of a suitable gelling agent; and
  c. about 0.001 to 0.5% by weight of a mixture of from 2 to 5 of said corticosteroids.

23. The composition of claim 20 which comprises a. about 0.5 to 2.0% by weight of carboxypolymethylene;
b. about 98 to 99.50% by weight of a solvent wherein said glycol is propylene glycol; and
c. about 0.005 to 0.2% by weight of a mixture of from 2 to 5 corticosteroids chosen from the group consisting of those represented by formulas A, C, D, E and F.

24. A topical, anti-inflammatory, pharmaceutical cream composition which comprises
0.0082 % by weight fluocinonide;
0.0039 % by weight fluocinolone acetonide-21-propionate;
0.0029 % by weight fluocinolone acetonide-21-cyclopropyl carboxylate;
4.00 % by weight Cetyl alcohol;
4.00 % by weight Stearyl alcohol;
2.00 % by weight Tween 60;
2.00 % by weight Span 60;
5.75 % by weight mineral oil;
30.00 % by weight propylene glycol; and
enough water to bring the total to 100.00.

25. The cream composition of claim 24 which comprises in addition 0.3500 % by weight neomycin base (as sulfate).

26. The cream composition of claim 24 which comprises in addition 0.2875 % by weight neomycin base (as sulfate), 0.0275 % by weight gramicidin, and $12 \times 10^6$ International Units mystatin.

27. A topical, anti-inflammatory pharmaceutical gel composition which comprises
0.012 % by weight fluocinonide
0.0056 % by weight fluocinolone acetonide 21-propionate;
0.0045 % by weight fluocinolone acetonide 21-cyclopropyl carboxylate,
0.50 % by weight CARBOPOL; and
enough solvent to bring the total to 100.00, said solvent comprising about 70 per cent by weight propylene glycol and 30 per cent by weight water.

28. A topical, anti-inflammatory, pharmaceutical ointment composition which comprises
0.0112 % by weight fluocinonide;
0.0042 % by weight fluocinolone acetonide-21-acetate;
0.0110 % by weight fluocinolone acetonide-21-cyclopropyl carboxylate;
8.00 % by weight mineral oil;
8.00 % by weight propylene glycol;
2.00 % by weight Tween 60;
2.00 % by weight Span 60; and
enough white petrolatum to bring the total to 100.00.

29. A process which comprises
dissolving at least two corticosteroids chosen from the group of corticosteroids represented by the formulas (A) through (K) as shown below in a suitable pharmaceutical solvent so that each corticosteroid is present in solution at its saturation solubility wherein in compound (A), R is $$-\overset{O}{\underset{\|}{C}}-CH_3,$$

In compound (B), R is H,
in compound (C), R is $$-\overset{O}{\underset{\|}{C}}-CH_2-CH_3,$$

in compound (D), R is $$-\overset{O}{\underset{\|}{C}}-\overset{CH_2}{\underset{CH-CH_2}{\diagup\diagdown}},$$

in compound (E), R is $$-\overset{O}{\underset{\|}{C}}-\overset{CH_2-CH_2}{\underset{CH-CH_2}{\diagup\diagdown}},$$

in compound (F), R is $$-\overset{O}{\underset{\|}{C}}-(CH_2)_3CH_3,$$

in compound (G), $R^1$ is F; X and $X^1$ both Cl, Z is a double bond;
in compound (H), $R^1$ is OH; X and $X^1$ are both Cl, Z is a double bond
in compound (I), $R^1$ is OH; X is H and $X^1$ is OH, Z is a single bond;
in compound (J), $R^1$ is $$O-\overset{O}{\underset{\|}{C}}-CH_3;$$

X is H, and $X^1$ is OH, Z is a double bond; and compound (K) is

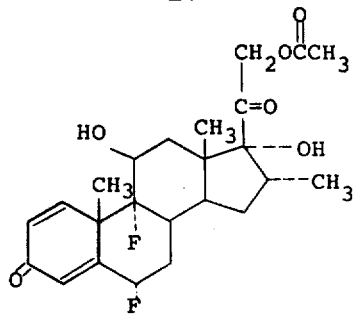

and mixing said resulting solution with an effective amount of suitable pharmaceutical formulation additives to form a topical, anti-inflammatory, pharmaceutical composition which comprises about 0.001% by weight to about 0.5% by weight of said corticosteroids.

30. The process of claim 29 wherein said solvent is a mixture comprising about 15% by weight glycol or more and 85% by weight or less water.

31. The process of claim 30 wherein said glycol is propylene glycol.

32. The process of claim 31 wherein said group consists of corticosteroids represented by formulas A,C,-D,E,F,G,H, J and K.

33. The process of claim 32 wherein said group consists of corticosteroids represented by formulas A,C,D,E and F.

34. The process of claim 33 wherein 3 corticosteroids are present in said composition.

35. The process of claim 29 wherein said solvent is a mixture of about 15% by weight or more propylene glycol and 85% by weight or less water and the resulting topical, anti-inflammatory, pharmaceutical composition comprises
   a. about 1.0 to 99.9% by weight of said pharmaceutically acceptable solvent,
   b. about 0.1 to 99% by weight suitable pharmaceutical additives, and
   c. about 0.005 to about 0.20% by weight of said corticosteroid mixture.

36. The process of claim 29 wherein said pharmaceutical composition is a cream formulation which comprises
   a. about 55 to 99% by weight solvent comprising
      i. 15% by weight or more of a glycol and
      ii. 85% by weight or less water, and
   b. suitable pharmaceutical additives comprising
      i. about 1 to 20% by weight fatty alcohol;
      ii. about 0 to 10% by weight non-ionic surfactant;
      iii. about 0 to 10% by weight mineral oil;
      iv. about 0 to 5% by weight typical pharmaceutical adjuvants.

37. The process of claim 29 wherein said pharmaceutical composition is an ointment formulation which comprises
   a. about 1 to 15% by weight of said pharmaceutically suitable solvent which is a glycol;
   b. suitable pharmaceutical additives comprising
      i. about 45 to 94% by weight white petrolatum;
      ii. about 5 to 20% by weight mineral oil;
      iii. about 0 to 10% by weight pharmaceutically acceptable surfactant; and
      iv. about 0 to 10% by weight stabilizer.

38. The process of claim 29 wherein said pharmaceutical composition is a gel formulation comprising
   a. about 90 to 99.9% by weight of a suitable solvent comprising about 15 to 90% by weight of a pharmaceutically acceptable glycol and about 10% to 85% by water;
   b. about 0.1 to 10% by weight of a suitable pharmaceutical formulation additive which is a gelling agent; and
   c. about 0.001 to 0.5% by weight of a mixture of from 2 to 5 of said corticosteroids.

39. A process of treating inflammatory conditions which comprises topically administering an effective amount of a composition which comprises
   a. a pharmaceutically acceptable solvent;
   b. suitable pharmaceutical formulation additives;
   c. at least two corticosteroids, each dissolved in said solvent at a concentration equal to the saturation solubility for each corticosteroid, said corticosteroids being chosen from the group consisting of those represented by the following formulas

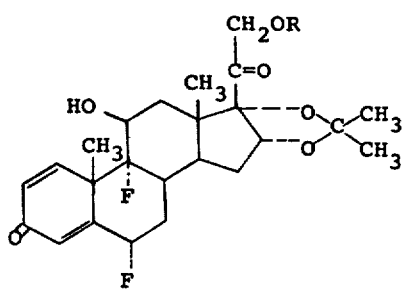

wherein in compound (A) R is

in compound (B) R is H
in compound (C) R is

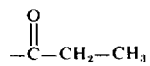

in compound (D) R is

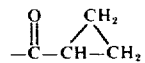

in compound (E) R is

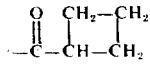

in compound (F) R is

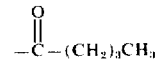

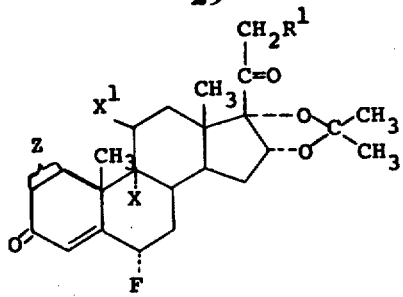

in compound (G) R¹ is F, X¹ are both Cl, Z is a double bond;
in compound (H) R¹ is OH, X and X¹ are both Cl, Z is a double bond;
in compound (I) R¹ is OH, X is H; and X¹ is OH, Z is a single bond;
in compound (J) R¹ is

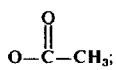

X is H, X¹ is OH, Z is a double bond; and compound (K) is

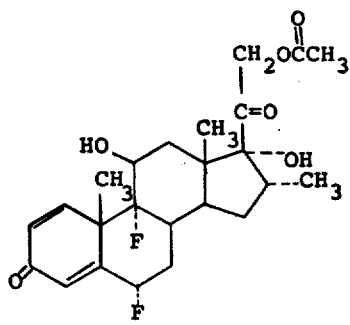

said corticosteroids being present at a total concentration of about 0.001% by weight to about 0.5% by weight.

40. The process of claim 39 wherein said solvent is a mixture comprising about 15% by weight glycol or more and 85% by weight or less water.

41. The process of claim 40 wherein said glycol is propylene glycol.

42. The process of claim 41 wherein said group consists of corticosteroids represented by formulas A, C, D, E, F, G, H, J and K.

43. The process of claim 42 wherein said group consists of corticosteroids represented by formulas A, C, D, E and F.

44. The process of claim 43 wherein 3 corticosteroids are present in said composition.

45. The process of claim 39 wherein said solvent is a mixture of about 15% by weight or more propylene glycol and 85% by weight or less water and the resulting topical, anti-inflammatory, pharmaceutical composition comprises
   a. about 1.0 to 99.9% by weight of said pharmaceutically acceptable solvent,
   b. about 0.1 to 99% by weight suitable pharmaceutical additives, and
   c. about 0.005 to about 0.20% by weight of said corticosteroid mixture.

46. The process of claim 39 wherein said composition is a cream formulation which comprises
   a. about 55 to 99% by weight solvent comprising
      i. 15% by weight or more of a glycol and
      ii. 85% by weight or less water, and
   b. suitable pharmaceutical additives comprising
      i. about 1 to 20% by weight fatty alcohol;
      ii. about 0 to 10% by weight non-ionic surfactant;
      iii. about 0 to 10% by weight mineral oil;
      iv. about 0 to 5% by weight typical pharmaceutical adjuvants.

47. The process of claim 39 wherein said pharmaceutical composition is an ointment formulation which comprises
   a. about 1 to 15% by weight of said pharmaceutically suitable solvent which is a glycol;
   b. suitable pharmaceutical additives comprising
      i. about 45 to 94% by weight white petrolatum;
      ii. about 5 to 20% by weight mineral oil;
      iii. about 0 to 10% by weight pharmaceutically acceptable surfactant; and
      iv. about 0 to 10% by weight stabilizer.

48. The process of claim 29 wherein said pharmaceutical composition is a gel formulation comprising
   a. about 90 to 99.9% by weight of a suitable solvent comprising about 15 to 90% by weight of a pharmaceutically acceptable glycol and about 10% to 85% by water;
   b. about 0.1 to 10% by weight of a suitable pharmaceutical formulation additive which is a gelling agent; and
   c. about 0.001 to 0.5% by weight of a mixture of from 2 to 5 of said corticosteroids.

49. The composition of claim 6 which comprises
   a. about 1 to 10% by weight of a suitable pharmaceutical solvent;
   b. about 1 to 10% by weight propylene carbonate;
   c. about 1 to 10% by weight of a suitable pharmaceutical surfactant;
   d. about 70 to 97% by weight white petrolatum; and
   e. about 0.001 to 0.5% by weight of said corticosteroids.

50. The composition of claim 49 which comprises
   a. about 2 to 6% by weight of a glycol solvent;
   b. about 1 to 4% by weight propylene carbonate;
   c. about 1 to 5% by weight of said surfactant;
   d. about 85 to 95% by weight white petrolatum; and
   e. about 0.005 to 0.2% by weight of a mixture of from 2 to 5 corticosteroids chosen from the group consisting of those represented by formulas A, C, D, E, and F.

* * * * *